United States Patent [19]

Brunck et al.

[11] Patent Number: 4,772,684

[45] Date of Patent: Sep. 20, 1988

[54] PEPTIDES AFFECTING BLOOD PRESSURE REGULATION

[75] Inventors: Terence K. Brunck; Clarence Colby, Jr., both of Alameda, Calif.

[73] Assignee: Triton Biosciences, Inc., Alameda, Calif.

[21] Appl. No.: 158,961

[22] Filed: Feb. 18, 1988

Related U.S. Application Data

[63] Continuation of Ser. No. 2,298, Jan. 20, 1987, which is a continuation-in-part of Ser. No. 830,795, Feb. 19, 1986, abandoned.

[51] Int. Cl.$^4$ ................................................ C07K 7/14
[52] U.S. Cl. ..................................................... 530/316
[58] Field of Search ......................................... 530/316

[56] References Cited

U.S. PATENT DOCUMENTS

| | | | |
|---|---|---|---|
| 3,915,946 | 10/1975 | Bumpus et al. | 260/112.5 |
| 3,915,948 | 10/1975 | Wille | 260/112.5 |
| 3,917,580 | 11/1975 | Bumpus et al. | 260/112.5 |
| 3,923,769 | 12/1975 | Bumpus et al. | 260/112.5 |
| 3,923,770 | 12/1975 | Bumpus et al. | 260/112.5 |
| 3,923,771 | 12/1975 | Bumpus et al. | 260/112.5 |
| 3,925,345 | 12/1975 | Bumpus et al. | 260/112.5 |
| 3,947,575 | 3/1976 | Ondetti | 424/177 |
| 3,973,006 | 8/1976 | Ondetti | 424/177 |
| 3,975,365 | 8/1976 | Mazur | 260/112.5 |
| 3,976,770 | 8/1976 | Bumpus et al. | 424/177 |
| 4,013,791 | 3/1977 | Wissmann et al. | 424/177 |
| 4,179,433 | 12/1979 | Kisfaludy et al. | 260/112.5 |
| 4,209,442 | 6/1980 | Kisfaludy et al. | 260/112.5 |
| 4,672,054 | 6/1987 | Kuprina et al. | 514/16 |

FOREIGN PATENT DOCUMENTS

| | | |
|---|---|---|
| 2758483 | 7/1979 | Fed. Rep. of Germany . |
| 209863 | 4/1980 | German Democratic Rep. . |
| 993864 | 7/1976 | Canada . |
| 687794 | 5/1981 | U.S.S.R. . |
| 891648 | 12/1981 | U.S.S.R. . |
| 8605208 | 9/1986 | World Int. Prop. O. . |

OTHER PUBLICATIONS

Khosla, et al. "Structure–Activity Relationship in Angiotensin II Analogs", *Angiotensin* I. H. Page, F. M. Bumpus Ed.; Handbook of Experimental Pharmacology, vol. 37, Springer, Berlin, 1974.

Chou, et al. "Monoclonal Antibodies to Human Myelin Basic Protein" *J. Neurochemistry*, 46 (1), 47–53 (1986).

*Primary Examiner*—Delbert R. Phillips
*Attorney, Agent, or Firm*—Karen B. Dow; Al A. Jecminek

[57] ABSTRACT

Peptides of the formula:

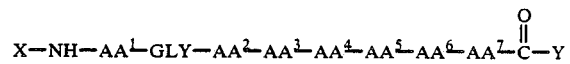

wherein:
NH is the α amino group of amino acid AA$^1$;

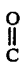

is the carbonyl group of amino acid AA$^7$;
X is H—,

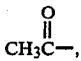

GLU-VAL-, or VAL-TYR-HIS-GLU-VAL;
Y is —OH, —NH$_2$, or —PRO; AA$^1$ is LYS, GLU, GLN, pGLU, βALA, PRO, PRO-OH, PIC, or AIB; AA$^2$ is VAL, LEU, ILE, MET, or AIB; AA$^3$ is ASP, TYR, GLU, HIS, or PHE; AA$^4$ is VAL, MET, ILE, LEU, or AIB; AA$^5$ is TYR, HIS, or GLU; AA$^6$ is ALA, PRO, SER, βALA, PRO-OH, or AIB; and AA$^7$ is VAL, LEU, ILE, or AIB;

and salts thereof are claimed as effective blood pressure regulators. Further provided, are antibodies to these peptides, as well as diagnostic and therapeutic methods for blood pressure regulation.

5 Claims, No Drawings

PEPTIDES AFFECTING BLOOD PRESSURE REGULATION

CROSS REFERENCE TO RELATED APPLICATIONS

This application is a continuation of copending application Ser. No. 002,298, filed on Jan. 20, 1987, which in turn is a continuation-in-part of Ser. No. 830,795, filed on Feb. 19, 1986, now abandoned.

BACKGROUND OF THE INVENTION

The regulation of blood pressure in mammals, especially humans, is an important medical problem. Hypertension, which is an abnormally high level of blood pressure, is a disease of particular concern, along with hypotension, which is low blood pressure. Therefore, the discovery of substances that can aid in the detection and treatment of blood pressure abnormalities is an important one. The present invention encompasses a class of peptides and their antibodies which affect the regulation of blood pressure.

A physiological pathway believed to affect blood pressure is as follows. Angiotensinogen also known as renin substrate, is acted upon by an enzyme, called renin, to produce angiotensin I. Angiotensin I is a relatively inactive decapeptide; in other words, angiotensin I does not have a major hormonal effect on blood pressure. However, angiotensin I is converted to angiotensin II by an enzyme called angiotensin converting enzyme. Angiotensin II, an octapeptide, is often at elevated levels in those individuals with hypertension and its action at these elevated levels causes blood vessel constriction and water retention, both of which are associated with hypertension. By modification or blockage of the peptides or enzymes in this pathway, the level of blood pressure can be controlled.

The pathway is also shown in the following diagram:

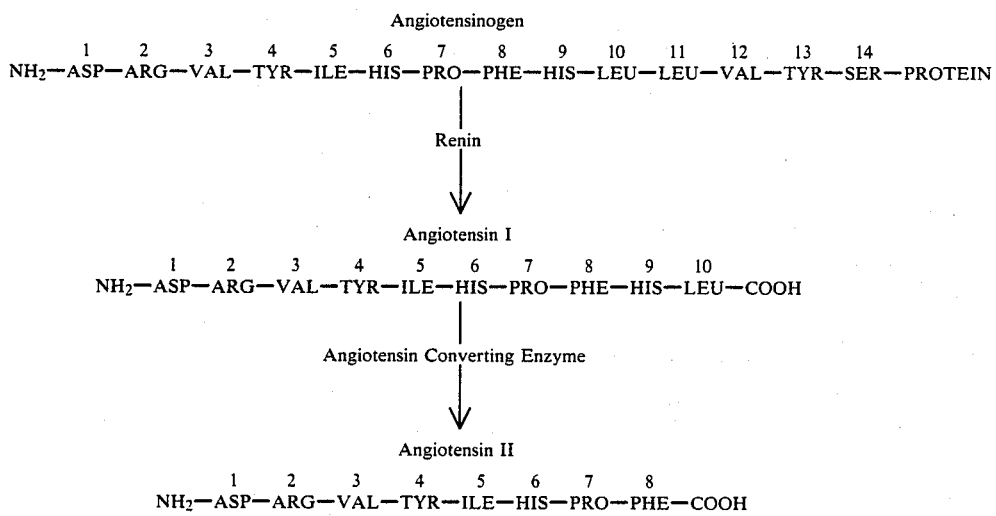

Various peptides or angiotensin analogs have been prepared and disclosed. An extensive review of known analogs is found in Khosla, et al., "Structure-Activity Relationship in Angiotensin II Analogs", *Angiotensin* (Page and Bumpus eds), Handbook of Experimental Pharmacology, Vol. 34, 126-161 (1974). Other analogs are described in U.S. Pat. No. 4,179,433 and 4,209,442, which analogs have the following amino acid sequence:

W-ARG-VAL-TYR-ILE-HIS-PRO-Z wherein:
W is a radical derived from an aliphatic α-aminooxycarboxylic acid, hydroxyacetyl, or a-hydroxypropyl; and
Z is a radical derived from an aliphatic α-amino-carboxylic acid, leucyl, isoleucyl, alanyl, or threonyl.

U.S. Pat. No. 4,302,386 describes the production of antibodies raised against hormones.

SUMMARY OF THE INVENTION

Peptides of the following formula are part of the present invention:

$$X-NH-AA^1-GLY-AA^2-AA^3-AA^4-AA^5-AA^6-AA^7-\overset{O}{\underset{\|}{C}}-Y$$

wherein:
NH is the α amino group of amino acid $AA^1$;

$\overset{O}{\underset{\|}{C}}$ is the carbonyl group of amino acid $AA^7$;
X is H—, $\overset{O}{\underset{\|}{CH_3C}}$—, GLU-VAL-, or
VAL-TYR-HIS-GLU-VAL-;
Y is —OH, —NH$_2$, or —PRO;
$AA^1$ is LYS, GLU, GLN, pGLU, βALA, PRO, PRO—OH, PIC, or AIB;
$AA^2$ is VAL, LEU, ILE, MET, or AIB;
$AA^3$ is ASP, TYR, GLU, HIS, or PHE;
$AA^4$ is VAL, MET, ILE, LEU, or AIB;
$AA^5$ is TYR, HIS, or GLU;
$AA^6$ is ALA, PRO, SER, βALA, PRO—OH, or AIB; and AA⁷ is VAL, LEU, ILE, or AIB;
as well as salts thereof.

Further provided by this invention are antibodies raised to these peptides, along with pharmaceutical compositions comprising a peptide or antibody and a pharmaceutically-acceptable carrier. In addition, this invention includes diagnostic and therapeutic methods for blood pressure regulation.

AA⁵ is TYR, HIS, or GLU;
AA⁶ is ALA, PRO, or SER; and
AA⁷ is VAL or LEU.

In addition to the peptides defined above, the following are preferred: wherein AA¹ is LYS; AA² is VAL; AA³ is TYR; AA⁴ is ILE; is HIS; AA⁶ is ALA; and AA⁷ is LEU. Also preferred are the following peptides:

| Peptide Number | SEQUENCE |
|---|---|
| 1 | NH₂—LYS—GLY—VAL—ASP—VAL—TYR—ALA—VAL—COOH |
| 2 | NH₂—LYS—GLY—VAL—TYR—ILE—HIS—ALA—LEU—COOH |
| 3 | NH₂—LYS—GLY—VAL—ASP—MET—HIS—ALA—LEU—COOH |
| 4 | GLU—VAL—LYS—GLY—VAL—TYR—ILE—HIS—ALA—LEU—COOH |
| 5 | VAL—TYR—HIS—GLU—VAL—LYS—GLY—VAL—TYR—ILE—HIS—ALA—LEU—COOH |
| 6 | NH₂—GLU—GLY—LEU—GLU—LEU—GLU—ALA—LEU—COOH |
| 7 | NH₂—LYS—GLY—VAL—TYR—ILE—HIS—ALA—LEU—CONH₂ |
| 8 | NH₂—LYS—GLY—VAL—TYR—ILE—HIS—ALA—LEU—PRO |
| 9 | $\overset{O}{\underset{\|}{CH_3C}}$NH—LYS—GLY—VAL—TYR—ILE—HIS—ALA—LEU—CONH₂ |
| 10 | $\overset{O}{\underset{\|}{CH_3C}}$NH—LYS—GLY—VAL—TYR—ILE—HIS—ALA—LEU—PRO and |
| 11 | NH₂—LYS—GLY—VAL—TYR—ILE—HIS—ALA—LEU—COOH (all D-form amino acids) |
| 12 | NH₂—GLN—GLY—VAL—ASP—VAL—HIS—PRO—VAL—COOH |
| 13 | NH₂—LYS—GLY—VAL—TYR—MET—HIS—SER—LEU—COOH |

DETAILED DESCRIPTION OF THE INVENTION

The following abbreviations are used throughout the specification. In the case of amino acids, an L-form is usually preferred, although the D-form or racemic mixtures of the amino acid may be used.

| | |
|---|---|
| SER: serine | PSS: physiological salt solution |
| LEU: leucine | TFA: trifluoroacetic acid |
| GLN: glutamine | Tos: p-toluenesulfonyl |
| GLU: glutamic acid | Boc: tert-butyloxycarbonyl |
| pGLU: pyroglutamic acid | Bzl: benzyl |
| LYS: lysine | Cl₂—Bzl: 2,6-dichlorobenzyl |
| PRO: proline | Cl—Z: 2-chlorobenzyloxycarbonyl |
| PRO—OH: hydroxyproline | DNA: deoxyribonucleic acid |
| VAL: valine | EBV: Epstein Barr Virus |
| HIS: histidine | KLH: Keyhole limpet hemocyanin |
| ASP: aspartic acid | RIA: radioimmunoassay |
| GLY: glycine | ELISA: enzyme-linked immunosorbent assay |
| ILE: isoleucine | |
| PIC: picolinic acid | EIA: enzyme immunoassay |
| ALA: alanine | DEAE: diethylaminoethyl |
| βALA: beta-alanine | Tris-HCl: tris (hydroxymethyl)-aminomethane hydrochloride |
| TYR: tyrosine | |
| PHE: phenylalanine | EDIA: ethylenediaminetetraacetate |
| MET: methionine | PCMS: para-chloromercurisulfate |
| ARG: arginine | βBzl: beta-benzyl |
| AIB: alpha-aminoisobutyric acid | BSA: bovine serum albumin |
| | DMSO: dimethylsulfoxide |
| DCM: dichloromethane | BrZ: 2-bromobenzyloxycarbonyl |
| HF: hydrogen fluoride | DICD: diisopropylcarbodiimide |
| HBr: hydrogen bromide | DIEA: diisopropylethylamine |
| HOAc: acetic acid | DMF: dimethylformamide |
| DCC: dicylohexyl-carbodiimide | HOBt: N—hydroxybenzotriazole |

Preferred are peptides wherein:
AA¹ is LYS, GLU, or GLN;
AA² is VA or LEU;
AA³ is ASP, TYR, or GLU;
AA⁴ is VAL, LET, ILE, or LEU;

The peptides of the present invention can be prepared by conventional processes for synthesizing peptides; more specifically, using processes as described in Schroder and Lubke, *The Peptides*, Vol. 1, published by Academic Press, New York (1966), or Izumiya, et al., *Synthesis of Peptides*, published by Maruzen Publishing Co., Ltd., (1975), both of which are herein incorporated by reference. For example, an azide process, an acid chloride process, an acid anhydride process, a mixed anhydride process, a DCC process, an active ester process (for example: p-nitrophenyl ester, N-hydroxysuccinimide ester, or cyanomethyl ester), a carbodiimidazole process, an oxidative-reductive process, or a DCC/additive process can be used. Solid phase and solution phase syntheses are both applicable to the foregoing processes.

The peptides of the present invention are suitable prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. (Amino groups that are not being used in the coupling reaction must be protected to prevent coupling at an incorrect location.)

In case that a solid phase synthesis is adopted, the C terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin; hydroxymethyl resins, phenol resins, tert-alkyloxycarbonylhydrazidated resins and the like.

An amino group-protected amino acid is bound in sequence through condensation of its activated carboxyl group and the reactive amino group of the previously formed peptide or chain, to synthesize step by step. After synthesizing the complete sequence the peptide is split off from the insolule carrier to produce the peptide. This solid-phase approach is generally described by Merrifield, et al. in *J. Am. Chem. Soc.* 85, 2149-2156 (1963), which is herein incorporated by reference.

The peptide can be cleaved and the protecting groups removed by either stirring the insoluble carrier or resin in anhydrous, liquid HF at about 0° C. for about 20 to 90 minutes, preferably 60 minutes or by bubbling HBr continuously through a 1 mg/10 ml suspension of the resin in TFA for 30 to 60 minutes at about room temperature, depending on the protecting groups selected. Other deprotection methods may also be used.

In the foregoing process, it is preferred that respective amino acids of histidine, tyrosine, glutamic acid, lysine, serine, and aspartic acid be protected at the side chain functional groups. These functional groups at the side chain are protected with ordinary protective groups which are split off after completion of the reaction. The functional groups that take part in the reaction are generally activated.

Examples of protective groups for amino groups include: benzyloxycarbonyl, Boc, tert-amyloxycarbonyl, isobornyloxycarbonyl, p-methoxybenzyloxycarbonyl, Cl-Z, adamantyloxycarbonyl, trifluoroacetyl, phthalyl, formyl o-nitrophenylsulfenyl, diphenylphosphinothioyl, and the like.

Examples of protective groups for the imino group of histidine include: Tos, Bzl, benzyloxycarbonyl, trityl, and the like.

Examples of protective groups for the hydroxy group of tyrosine include: Bzl, $Cl_2$-Bzl, BrZ, benzyloxycarbonyl, acetyl, Tos, and the like.

Examples of protective groups for the amino group of lysine include: benzyloxycarbonyl, Cl-Z, $Cl_2$-Bzl, Boc, Tos, and the like.

Protection for the carboxyl groups of glutamic acid and aspartic acid includes: esterification of the carboxylic acids with benzyl alcohol, methanol, ethanol, tert-butanol, and the like.

Examples of protective groups for the hydroxy of serine include: Bzl, tert-butyl, and the like.

Examples of activated carboxyl groups include: the corresponding acid chlorides, acid anhydrides, mixed acid anhydrides, azides, and active esters (esters with pentachlorophenol, p-nitrophenol, N-hydroxysuccinimide, N-hydroxybenzotriazole, N-hydroxy 5-norbornene-2,3-dicarboxydiimide, and the like).

In the foregoing process, the residues PIC and pGLU may only be used as the amino terminus of the final peptide. Furthermore, the residue AIB is often coupled to the growing peptide chain in a solvent mixture which is about one part DMSO to about one part DMF.

The peptides of this invention can also be prepared through DNA techniques. When the peptide contains only naturally occuring amino acids, the amino acid sequence of the desired peptide is used to deduce the codon sequence for the single-stranded DNA, synthesized using conventional synthetic techniques, then the double-stranded DNA is prepared and inserted at a suitable site in a cloning vehicle, vector, or plasmid. An appropriate organism, such as bacteria cells, yeast cells, or mammalian cells, is transformed to obtain expression of the desired peptide.

The prepared peptides of the present invention can be isolated and purified from the reaction mixture by means of peptide separation, for example, by extraction, counter-current distribution, column chromatography, high performance liquid chromatography, and the like.

The peptides of this invention form salts with a variety of inorganic or organic bases. The non-toxic, pharmaceutically-acceptable salts are preferred, although other salts are also useful in isolating or purifying the product. Such pharmaceutically-acceptable salts include metal salts, such as sodium, potassium, or lithium, alkaline earth metal salts, such as calcium or magnesium, and salts derived from amino acids, such as arginine or lysine. The salts are obtained by reacting the acid form of the peptide with an equivalent of the base supplying the desired ion in a medium in which the salt precipitates or in aqueous medium and then lyophilizing.

Similarly, the peptides form salts with a variety of inorganic and organic acids. Again, the non-toxic, pharmaceutically-acceptable salts are preferred, although other salts are also useful in isolating or purifying the product. Such pharmaceutically-acceptable salts include those formed with hydrochloric acid, methanesulfonic acid, sulfuric acid, maleic acid, and the like. The salts are obtained by reacting the product with an equivalent amount of the acid in a medium in which the salt precipitates.

Antigens can be prepared by using the peptides or fragments of the peptides of the present invention as haptens and reacting the peptides or fragments with a suitable carrier in the presence of a hapten-carrier binding agent. In this case, natural and synthetic proteins having a high molecular weight, which are conventionally employed in the preparation of antigens, can be employed as carriers to be bound to the haptens. Examples of such carriers include: albumins of animal sera, globulins of animal sera, thyroglobulins of animals, hemoglobulins of animals, hemocyanins of animals, such as KLH, proteins extracted from ascaris, polylysine, polyglutamic acid, lysine-glutamic acid copolymers, and copolymers containing lysine or ornithine.

As hapten-carrier binding agents, those conventionally employed in the preparation of antigens can be employed. Specific examples of these agents include: diazonium compounds for cross linking, aliphatic dialdehydes for cross linking an amino group with an amino group, dimaleimide compounds for cross linking a thiol group with a thiol group, maleimidocarboxyl-N-hydroxysuccinimide esters for cross linking an amino group with a thiol group, and agents used in conventional peptide bond forming reactions in which amide bonds are formed from an amino group and a carboxyl group. Also as the hapten-carrier binding agent, it is also possible to use diazonium aryl carboxylic acids, such as p-diazonium phenylacetic acid, in combination with conventional peptide bond-forming agents, such as the dehydrating and condensing agents described above.

The coupling reaction for preparing the antigenic forms of the peptides of the present invention is suitably carried out in an aqueous solution or a conventional buffer solution having a pH of 7 to 10, preferably in a buffer solution having a pH of 8 to 9, at temperatures of about 0° to 40° C., preferably around room temperature.

The coupling reaction is generally completed within about 1 to about 24 hours, preferably 3 to 5 hours. Representative examples of buffer solutions which can be used in the above process include:

0.2 N sodium hydroxide-0.2 M boric acid-0.2 M potassium chloride buffer solution;

0.2 M sodium carbonate-0.2 M boric acid-0.2 M potassium chloride buffer solution;

0.05 M sodium tetraborate-0.2 M boric acid-0.05 M sodium chloride buffer solution; and 0.1 M dihydrogen potassium phosphate-0.05 M sodium tetraborate buffer solution.

Proportions of the hapten, hapten-carrier binding agent, and carrier can be appropriately determined, but it is preferred that the molar ratio of hapten to carrier be about 1 to about 20, preferably about 10, and the molar ratio of binding agent to hapten be about 1 to about 10, preferably about 2 to about 5. In the coupling reaction, the carrier is bound to the hapten via the hapten-carrier binding agent to obtain a desired antigen composed of a peptide-carrier complex.

After completion of the coupling reaction, the antigen can easily be isolated and purified by means of dialysis, gel filtration, fractionation precipitation, and the like.

The antibody or antibodies of the present invention which are raised to a peptide or peptides of this invention, can be monoclonal or polyclonal, but monoclonal is preferred. In general, antibodies may be obtained by injecting the desired immunogen or antigen into a wide variety of vertebrates in accordance with conventional techniques. Suitable vertebrates include mice, rats, sheep, and goats, with mice being preferred. Usually, the animals are bled periodically with the successive bleeds having improved titer and specificity. The antigens may be injected intramuscularly, intraperitoneally, subcutaneously, or the like.

Polyclonal antibodies are prepared by hyperimmunization of the animal with antigen. Then the blood of the animal is collected shortly after the repeated immunizations and the gamma globulin is isolated. Suitable methods for preparing polyclonal antibodies are described in the *Handbook of Experimental Immunology*, 3d edition, (ed. Weir, 1978), which is herein incorporated by reference.

To obtain monoclonal antibodies, spleen cells from the immunized vertebrate demonstrating the desired antibody response are immortalized. The manner of immortalization is not critical, but the most common method is fusion with a myeloma fusion partner. Other techniques of immortalization include EBV transformation, transformation with bare DNA, such as oncogenes or retroviruses, or any other method which provides for stable maintenance of the cell line and production of monoclonal antibodies. The general process for obtaining monoclonal antibodies is described by Kohler and Milstein, in *Nature*, 256, 495–497 (1975), which is herein incorporated by reference. Human monoclonal antibodies may be obtained by fusion of the spleen cells with an appropriate human fusion partner, such as WI-L2, described in European Application No. 82.301103.6, the relevant portions of which are herein incorporated by reference. A detailed technique for producing mouse x mouse monoclonal antibodies is taught by Oi and Herzenberg, in *Selected Methods in Cellular Immunology*, 351–372 (eds. Mishell and Shiigi, 1980), which also is herein incorporated by reference. The resulting hybridomas are screened to isolate individual clones, each of which secretes a single antibody species to the antigen.

The peptides and/or antibodies may be used without modification or may be modified in a variety of ways, for example, by labeling such as joining, either covalently or non-covalently, a moiety which directly or indirectly provides for a means of detection. A wide variety of labels are known and include: radionuclides, enzymes, substrates, cofactors, inhibitors, fluorescers, chemiluminescers, magnetic particles, and the like.

Many of the techniques for linking the peptides to suitable labels involve the use of activated carboxyl groups, either through the use of carbodiimide or active esters to form peptide bonds; the formation of thioethers by reaction of a mercapto group with an activated halogen, such as chloroacetyl; or activated olefin, such as maleimide, or the like.

The peptides and/or antibodies may be used in assays, which are homogeneous (without a separation step between free reagent and receptor-ligand complex) or heterogeneous (with a separation step between free reagent and receptor-ligand complex). Various commercial assays exist, such as RIA, ELISA, EIA, and the like. Usually, the assays detect the presence of a related antibody or antigen in a physiological fluid, such as urine, serum, plasma, and the like. For example, unlabeled antibodies can be employed by employing a second antibody, which is labeled and recognizes the antibody to a subject peptide. In a related application, the peptides and/or antibodies may be used to characterize the cell surface receptor.

Where the antigen may not be found in a physiological fluid or if found there is not diagnostic, then cells will have to be isolated and the cells assayed for the presence of the antigen. For detecting the antigen, the tissue sample may be lysed by conventional methods using bases, detergents, or the like, cellular debris separated by filtration or centrifugation, and the filtrate or supernatant isolated and assayed.

Frequently, the reagents are supplied in diagnostic kits, so as to optimize the sensitivity of the assay. For the subject invention, depending upon the nature of the assay, the protocol, and the label; either labeled or unlabeled antibody, or labeled peptide is provided, usually in conjunction with other additives, such as surface-active agents, buffers, stabilizers, materials necessary for signal production, such as substrates for enzymes, and the like.

The peptides of this invention and their antibodies can be used to reduce or increase blood pressure depending upon their respective antagonistic or agonistic properties. Therefore, hypertension or hypotension can be diagnosed or treated depending upon the peptide or antibody selected and the concentrations utilized. Typically, the human or other mammal being treated with the peptide or antibody is one that has been diagnosed as having blood pressure regulation needs, hypertension or hypotension. Therefore, the patient to be treated is in need of treatment due to an existing condition.

Methods and compositions employing the peptides of the invention, or antibodies, are also a part of this invention. In particular, therapeutic compositions comprise effective amounts of the peptides or antibodies in admixture with pharmaceutically- or physiologically-acceptable carriers. Pharmaceutical compositions that contain the polypeptides or antibodies as an active ingredient will normally be formulated with an appropriate solid or liquid carrier depending upon the particular mode of administration being used. For instance, parenteral formulations are usually injectable fluids that use pharmaceutically- or physiologically-acceptable fluids, such as physiological saline, balanced salt solutions, or the like, as a vehicle. Other drug delivery systems that may be used include: liposomes, biodegradable or bioerodible polymers, polyethylene glycol, and the like.

Also a part of this invention are methods of regulating or aiding in the regulation of the blood pressure of a mammalian host which comprises administering to the host an effective amount of a peptide or antibody described above. Usually, the host being treated is human and this human host is diagnosed as having hypertension, hypotension, or another blood pressure regulation abnormality. In the therapeutic methods of the invention, the peptides or antibodies may be administered to a human or any other mammalian host in various manners, such as orally, topically, intranasally, and parenterally, which includes: intravenously, intramuscularly, intraperitoneally, intradermally and subcutaneously. The particular mode of administration and dosage regimen will be selected by the skilled artisan taking into account the particulars of the patient and the nnature of treatment required. For example, dosages of about 0.1 to 50 mg/kg of body weight per day of active ingredient should be appropriate to alter blood pressure. Preferably, the dosage should be from about 0.1 to about 10 mg/kg.

The peptide or antibody therapy of the invention may be combined with other treatments and may be combined with or used in association with other chemotherapeutic or chemopreventive agents. For example, the peptides or antibodies can be formulated in combination with a beta-adrenergic blocker, a diuretic, or an angiotensin converting enzyme inhibitor, for the treatment of hypertension. Examples of beta-adrenergic blockers that can be used include: propranolol, practolol, acebutolol, timolol, and the like. Exemplary of the diuretics contemplated for use in combination with a peptide of this invention are the thiazide diuretics, as well as ethacrynic acid, ticrynafen, chlorthalidone, furosemide, musolimine, bumetanide, triamterene, amiloride, and spironolactone and salts of such compounds. Examples of angiotensin converting enzyme inhibitors include enalapril and captopril.

In addition, the peptides may be used in combination with adjuvants to generate vaccines. In this way, the immune system of an organism may be used to moderate the biological response of its hormone systems. The presentation of antigen may require special modifications to ensure the highest population of antibodies that give the desired biological responses.

The following examples are illustrative of the present invention, but are not to be construed as limitations on it.

EXAMPLE 1

Peptide Preparation

All peptide molecules were prepared on an automated peptide synthesizer (Beckman 990C) using Boc solid phase synthetic chemistry essentially as described by Merrifield and others [Merrifield, et al., *J. Am. Chem. Soc.*, 85, 2149 (1963); Erickson, et al., *Proteins* (3rd Ed.) 2, 2156 (1976); and Stewart, et al., *Solid Phase Peptide Synthesis*, Pierce Chemical Company, Rockford, IL (1984)]. The octapeptide, NH$_2$- LYS-GLY-VAL-ASP-VAL-TYR-ALA-VAL-COOH, designated as Peptide 1, was synthesized as follows.

N$^\alpha$-Boc-L-Val esterified to a benzyl moiety on polystyrene/divinylbenzene copolymer (1% crosslink, 0.6 meq/g), was used as the starting resin. Other N$^\alpha$-Boc protected amino acids with appropriate side-chain functional group protection were also used during the synthesis. The reagents were used as received, except DIEA and TFA were distilled before use.

Beginning with one gram of Boc-L-Val resin in the automated peptide synthesizer, the following double coupling protocol was used.

| | | |
|---|---|---|
| 1. | Resin wash, DCM | 3 times (×) @ 2 min |
| 2. | Boc removal, TFA/DCM/anisole (45:50:5) | 1 × 1 min<br>1 × 20 min |
| 3. | Resin wash, DCM | 3 × @ 2 min |
| 4. | Neutralization, DIEA/DCM (1:9) | 2 × @ 5 min |
| 5. | Resin wash, DCM | 3 × @ 3 min |
| 6. | Add Boc-amino acid/HOBt (1.25/1.0, 50% DCM/DMF) | 0.5 min |
| 7. | Add DICD (0.5 M/DCM) | 0.5 min |
| 8. | Mix | 30 min |
| 9. | Resin wash, DCM | 3 × @ 2 min |
| 10. | Neutralize, DIEA/DCM (1:9) | 2 × @ 5 min |
| 11. | Resin wash | 3 × @ 2 min |
| 12. | Add Boc-amino acid/HOBt (1.25/1.0, 50% DCM/DMF) | 0.5 min |
| 13. | Add DICD (0.5 M/DCM) | 0.5 min |
| 14. | Mix | 30 min |
| 15. | Resin wash, DCM | 3 × @ 2 min |
| 16. | To step #2, repeat | |

Subsequent residues were attached following the same procedure in accordance with the desired sequence. For this example the following protected amino acids wre used: N$^\alpha$-Boc-4-bromobenzyloxycarbonyl-L-tyrosine (N$^\alpha$-Boc-(BrZ)-L-tyrosine), N$^\alpha$-Boc-L-valine, N$^\alpha$-Boc-beta-benzyl-L-aspartic acid (N$^\alpha$-Boc-($\beta$Bzl)-L-aspartic acid), N$^\alpha$-Boc-L-valine, Boc-glycine, and N$^\alpha$-Boc-N'-2-chlorobenzyloxycarbonyl-L-lysine (N$^\alpha$-Boc-(N$^\alpha$-Cl-Z)-L-lysine) to give the Boc protected peptide resin. The final Boc group was removed by washing with DCM then exposing to TFA/anisole/DCM. The finished protected peptide resin was washed thoroughly with DCM (four times) and dried under vacuum for about 16 hours to remove traces of solvent.

The completed octapeptide was cleaved from the resin with simultaneous removal of side-chain protecting groups by treatment with anhydrous HF, in the presence of 10% (v/v) anisole for 60 min at 0° C. The HF/anisole was removed by water aspiration; and the resin wash was thoroughly dried under vacuum to remove trace amounts of HF. The peptide was washed from the resin with 15–20 ml portions of DMF, DMF/H$_2$O (9:1), DMF/H$_2$O (1:9), 10% HOAC/H$_2$O, and water. The combined washings were concentrated in vacuo and lyophilized to give a crude peptide powder.

The crude peptide material was purified by reverse phase high performance liquid chromatography using a preparative column (2.2×50 cm, Whatman Partisil 10 ODS-3); solvent A was 0.05% TFA/distilled water and solvent B was 0.05% TFA/acetonitrile. A typical purification chromatogram incorporated gradient development from 10 to 90% solvent B over 80 minutes at a flow rate of 10 ml/min to give purified peptide eluting at 34% solvent B.

In addition to Peptide 1, the following peptides of this invention were prepared using the general procedure described above:

| Peptide Number | SEQUENCE |
|---|---|
| 2 | NH₂—LYS—GLY—VAL—TYR—ILE—HIS—ALA—LEU—COOH |
| 3 | NH₂—LYS—GLY—VAL—ASP—MET—HIS—ALA—LEU—COOH |
| 4 | GLU—VAL—LYS—GLY—VAL—TYR—ILE—HIS—ALA—LEU—COOH |
| 5 | VAL—TYR—HIS—GLU—VAL—LYS—GLY—VAL—TYR—ILE—HIS—ALA—LEU—COOH |
| 6 | NH₂—GLU—GLY—LEU—GLU—LEU—GLU—ALA—LEU—COOH |
| 7 | NH₂—LYS—GLY—VAL—TYR—ILE—HIS—ALA—LEU—CONH₂ |
| 8 | NH₂—LYS—GLY—VAL—TYR—ILE—HIS—ALA—LEU—PRO |
| 9 | CH₃C(=O)NH—LYS—GLY—VAL—TYR—ILE—HIS—ALA—LEU—CONH₂ |
| 10 | CH₃C(=O)NH—LYS—GLY—VAL—TYR—ILE—HIS—ALA—LEU—PRO |
| 11 | NH₂—LYS—GLY—VAL—TYR—ILE—HIS—ALA—LEU—COOH (all D-form amino acids) |

EXAMPLE 2

Effects of Peptides on the Binding of Radiolabeled Angiotensin II to its Receptor Inhibition of angiotensin II binding to angiotensin II receptors by peptides of this invention was measured through the use of radioactive angiotensin II. Rabbit livers were homogenized and centrifuged in order to isolate particles sedimenting between 1,000 and 100,000×g. A portion of the particles which binds angiotensin II was solubilized with 1% digitonin, followed by ammonium sulfate fractionation between 49 and 65% saturation, followed by DEAE-cellulose chromatography at pH 7.5 using a linear gradient between 0.0 and 0.3 M KCl. The partially purified, solubilized receptor preparation bound 17 pmoles of angiotensin II per mg of protein when analyzed by Scatchard analysis, indicating a purity of approximately 0.1%.

The assay for binding of angiotensin II to the receptor was as follows: The complete system (150 μl) contained 30 mM Tris-HCl, pH 7.5, 2.5 mM K₂EDTA, 0.2 mM PCMS, 0.25 nM [¹²⁵I]angiotensin II (ca. 100,000 cpm), 100 μg BSA, 0.25% (v/v) Brij 99 (a polyoxyethylene ether of a fatty alcohol) and 30 μg of partially purified receptor. The reaction was initiated by addition of the receptor and samples were incubated for 60 minutes at 20° C. The reaction was terminated with 1 ml of cold 0.5% charcoal/0.05% dextran in 100 mM Tris-HCl, pH 7.5. Tubes were vortexed and then allowed to stand 10 minutes at 4° C., after which they were centrifuged and their supernatants, containing protein-bound angiotensin II, were counted.

The complete system under these conditions regularly yields about 10,000 cpm of bound radioactivity. A control, which lacks receptor, yields values of 50–200 cpm, which were subtracted from these data. Values of 50–200 cpm were obtained when 10 μM cold angiotensin II was present in the reaction mixture, indicating that virtually all binding was specific. A sample including 20 nM cold angiotensin II was also run. Residual binding of radioactivity in this control was 35–45%. Certain peptides of this invention were dissolved in water, except for Peptide 5, which was dissolved in 3% DMSO, 0.04 M acetic acid, and 0.05 M HCl in water. Results of these assays are given in Table 1.

TABLE 1
Inhibition by Peptides on Angiotensin II Binding to Isolated Hepatic Receptor

| Peptide | ID₅₀ (nM)ᵃ |
|---|---|
| Angiotensin II | 12–15 |
| 1 | 4,000 |
| 2 | 8–14 |
| 3 | 5,000 |
| 4 | 490 |
| 5 | 40 |
| 7 | 40–160 |
| 8 | 7–40 |
| 9 | 2,400–3,100 |
| 10 | 300–1,350 |
| 11 | >10,000 |
| 12 | 5,000 |
| 13 | 6 |

ᵃID₅₀ is the concentration of peptide that inhibited binding of radiolabeled angiotensin II by 50%.

This experiment demonstrates that peptides of this invention can inhibit the binding of angiotension II to its receptor.

EXAMPLE 3

Effects of Peptides on Arterial Smooth Muscle Contraction

The peptides of this invention were tested in vitro, using an assay of isolated rabbit aorta strips mounted in a muscle bath.

The left anterior descending coronary artery was excised from the heart and cut helically into a strip under a dissecting microscope. Strips were mounted vertically on a glass holder in a tissue bath containing 50 ml of PSS. The upper end of each strip was connected to a force transducer. The bathing medium was maintained at 37° C. and aerated with a mixture of 95% O₂–5% CO₂. The pH of the PSS was 7.2 and the composition, in mmoles/l, was as follows: NaCl 130, KCl 14.7, KH₂PO₄ 1.18, MgSO₄7H₂O 1.17, CaCl₂–2H₂O 1.6, NaHCO₂ 14.9, dextrose 5.5, and CaNa₂EDTA 0.03. In all experiments, the passive force on each strip was adjusted to 2,000 mg.

In one set of experiments, peptides were tested for ability to stimulate contractile response. Peptide was added to the bath in a step-wise, cumulative manner. Three peptides were tested: angiotensin II., Peptide 2 and Peptide 5. Muscle strips from between 2 and 6 rabbits were used to test each peptide. Results are given as average baseline response (Response −2,000 mg; (passive force)); and are shown in Tables 2, 3, and 4.

TABLE 2

Contractile Response to Angiotensin II (AII)

| [AII] (M) | Average Baseline Response (mg) |
|---|---|
| $10^{-11}$ | 0 |
| $3 \times 10^{-11}$ | 0 |
| $10^{-10}$ | 0 |
| $3 \times 10^{-10}$ | 991 |
| $10^{-9}$ | 1,726 |
| $3 \times 10^{-9}$ | 2,332 |
| $10^{-8}$ | 2,562 |
| $3 \times 10^{-8}$ | 2,613 |

TABLE 3

Contractile Response to Peptide 5

| [Peptide 5] (M) | Average Baseline Response (mg) |
|---|---|
| $3 \times 10^{-10}$ | 0 |
| $10^{-9}$ | 0 |
| $3 \times 10^{-9}$ | 50 |
| $10^{-8}$ | 245 |
| $3 \times 10^{-8}$ | 540 |
| $10^{-7}$ | 1,070 |
| $3 \times 10^{-7}$ | 1,230 |
| $10^{-6}$ | 1,380 |
| $3 \times 10^{-6}$ | 1,380 |

TABLE 4

Contractile Response to Peptide 2

| [Peptide 2] (M) | Average Baseline Response (mg) |
|---|---|
| $3 \times 10^{-10}$ | 0 |
| $10^{-9}$ | 0 |
| $3 \times 10^{-9}$ | 0 |
| $10^{-8}$ | 0 |
| $3 \times 10^{-8}$ | 0 |
| $10^{-7}$ | 0 |
| $3 \times 10^{-7}$ | 0 |
| $10^{-6}$ | 0 |

These experiments demonstrate that Peptide 5 of this invention can stimulate contraction of arterial smooth muscle.

In another set of experiments, the ability of peptides to increase or decrease contraction caused by angiotensin II was measured.

The muscle strips were bathed in PSS containing AII, $10^{-9}$M. Strips were allowed to contract until a steady-state contraction was reached (~8 minutes), then peptide was added in a step-wise. cumulative manner. The change in muscle strip contraction was measured after each addition of peptide, and more peptide was not added until contraction had stabilized from the previous peptide addition (10–15 minutes). Each peptide was tested in strips from 2 or 4 rabbits. Results are given as percentage (%) change from AII contractile response, and are shown in Tables 5 through 9.

A positive value indicates increased contraction, while a negative value represents a decreased contractile response.

TABLE 5

Peptide 2 Effect on AII-stimulated Contraction

| [Peptide 2] (M) | % Change from AII Response |
|---|---|
| $10^{-6}$ | 0 |
| $3 \times 10^{-6}$ | 0 |
| $10^{-5}$ | −18 |
| $3 \times 10^{-5}$ | −73 |
| $10^{-4}$ | −83 |

TABLE 6

Peptide 5 Effect on AII-stimulated Contraction

| [Peptide 5] (M) | % Change from AII Response |
|---|---|
| $3 \times 10^{-8}$ | 0 |
| $10^{-7}$ | +4 |
| $3 \times 10^{-7}$ | +24 |
| $10^{-6}$ | +36 |
| $3 \times 10^{-6}$ | +40 |
| $10^{-5}$ | −6 |
| $3 \times 10^{-5}$ | −28 |
| $10^{-4}$ | −38 |

TABLE 7

Peptide 8 Effect on AII-stimulated Contraction

| [Peptide 8] (M) | % Change from AII Response |
|---|---|
| $10^{-6}$ | 0 |
| $3 \times 10^{-6}$ | −8 |
| $10^{-5}$ | −9 |
| $3 \times 10^{-5}$ | −11 |
| $10^{-4}$ | −21 |

TABLE 8

Peptide 10 Effect on AII-stimulated Contraction

| [Peptide 10] (M) | % Change from AII Response |
|---|---|
| $3 \times 10^{-6}$ | 0 |
| $10^{-5}$ | +5 |
| $3 \times 10^{-5}$ | +34 |
| $10^{-4}$ | +85 |

TABLE 9

Peptide 11 Effect on AII-stimulated Contraction

| [Peptide 11] (M) | % Change from AII Response |
|---|---|
| $10^{-6}$ | 0 |
| $3 \times 10^{-6}$ | −3 |
| $10^{-5}$ | −5 |
| $3 \times 10^{-5}$ | −7 |
| $10^{-4}$ | −33 |

These experiments demonstrate that peptides of this invention can either increase or decrease contraction of arterial smooth muscle caused by angiotensin II.

In a third type of experiment, the ability of saralasin to block AII contraction and peptide-stimulated contraction was tested. The muscle strips were bathed in AII, $10^{-9}$ M. Once a steady contraction was established, saralasin, $10^{-8}$ M, was added to the bath. The addition of saralasin decreased AII contraction. Upon restabilization of the contractile response, Peptide 5, $10^{-6}$ M was added to the bath. No change in contractile response was seen.

This experiment demonstrates that contraction caused by peptides of this invention can be inhibited by a competitive antagonist for angiotensin II-stimulated contraction.

EXAMPLE 4

Effects of Peptides on Venous Smooth Muscle Relaxation

Peptide 2 of this invention was tested in vitro, using an assay of isolated dog venous strips mounted in a muscle bath. Isolated segments of the dog femoral vein (n=2) were mounted in organ baths for measurement of isometric force generation. The conditions were as described in Example 3. The vascular segments were made to contract in response to prostaglandin $F_{2a}$ ($8.5 \times 10^{-7}$M). After the contraction reached a plateau, angiotensin II ($3 \times 10^{-7}$M) was added to the organ bath and the venous segments relaxed to approximately 50% of the response to prostaglandin $F_{2a}$. This relaxation response to angiotensin II was inhibited 100% by saralasin ($10^6$M) and by Peptide 2 ($10^{-5}$M).

These experiments demonstrate that peptides of this invention can inhibit angiotensin II-caused relaxation of venous smooth muscles.

EXAMPLE 5

Effects of Peptides on Blood Pressure

Peptide 2 of this invention was tested in vivo, using a rat hypertension model. Adult male rats (n=4) were anesthetized with sodium pentobarbital (50 mg/kg) and the left jugular vein was cannulated for infusion of drugs. Bolus injections of angiotensin II were delivered via the same venous catheter. The right carotid artery was cannulated for measurement of blood pressure. Injection of angiotensin II (1 ng) caused an increase in mean arterial blood pressure (~50 mm Hg). Constant infusion of saralasin (1 mg/min) inhibited the pressor activity of angiotensin II. Infusior of Peptide 2 (0.1 to 0.5 mg/min) did not alter baseline blood pressure and did not influence pressor responses to angiotensin II.

We claim:

1. A peptide of the formula:

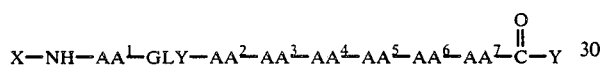

wherein:
NH is the α amino group of amino acid $AA^1$;

is the carbonyl group of amino acid $AA^7$;
x is H—,

GLU—VAL—, or
VAL—TYR—HIS—GLU—VAL—;
Y is —OH, —NH$_2$, or —PRO;
$AA^1$ is LYS, GLU, GLN, pGLU, βALA, PRO, PRO—OH, PIC, or AIB;
$AA^2$ is VAL, LEU, ILE, MET, or AIB;
$AA^3$ is ASP, TYR, GLU, HIS, or PHE;
$AA^4$ is VAL, MET, ILE, LEU, or AIB;
$AA^5$ is TYR, HIS, or GLU;
$AA^6$ is ALA, PRO, SER, βALA, PRO—OH, or AIB; and
$AA^7$ is VAL, LEU, ILE, or AIB;
or a salt thereof.

2. The peptide of claim 1 wherein:
$AA^1$ is LYS, GLU, or GLN;
$AA^2$ is VAL or LEU;
$AA^3$ is ASP, TYR, or GLU;
Xus G—,

GLU—VAL—, or
VAL—TYR—HIS—GLU—VAL—;
$AA^4$ is VAL, MET, ILE, or LEU;
$AA^5$ is TYR, HIS, or GLU;
$AA^6$ is ALA, PRO, or SER; and
$AA^7$ is VAL or LEU.

3. The peptide of claim 2 wherein:
$AA^1$ is LYS;
$AA^2$ is VAL;
$AA^3$ is TYR;
$AA^4$ is ILE;
$AA^5$ is HIS;
$AA^6$ is ALA; and
$AA^7$ is LEU.

4. The peptide of claim 1 which is selected from one of the following:
NH$_2$-LYS-GLY-VAL-ASP-VAL-TYR-ALA-VAL-COOH;
NH$_2$-LYS-GLY-VAL-TYR-ILE-HIS-ALA-LEU-COOH;
NH$_2$-LYS-GLY-VAL-ASP-MET-HIS-ALA-LEU-COOH;
GLU-VAL-LYS-GLY-VAL-TYR-ILE-HIS-ALA-LEU-COOH;
VAL-TYR-HIS-GLU-VAL-LYS-GLY-VAL-TYR-ILE-HIS-ALA-LEU-COOH;
NH$_2$-GLU-GLY-LEU-GLU-LEU-GLU-ALA-LEU-COOH;
NH$_2$-LYS-GLY-VAL-TYR-ILE-HIS-ALA-LEU-CONH$_2$;
NH$_2$-LYS-GLY-VAL-TYR-ILE-HIS-ALA-LEU-PRO;

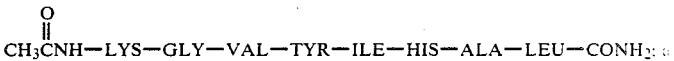

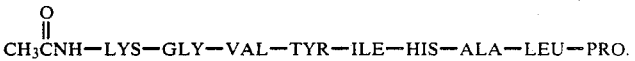

5. The peptide of claim 4 which is:
NH$_2$-LYS-GLY-VAL-TYR-ILE-HIS-ALA-LEU-COOH.

* * * * *

UNITED STATES PATENT AND TRADEMARK OFFICE
CERTIFICATE OF CORRECTION

PATENT NO. : 4,772,684

DATED : September 20, 1988

INVENTOR(S) : Terence K. Brunck and Clarence Colby, Jr.

It is certified that error appears in the above-identified patent and that said Letters Patent is hereby corrected as shown below:

Column 2, line 8, "a-hydroxypro" should read --$\alpha$-hydroxypro--. Column 3, line 66, "VA" should read --VAL--; line 68, "LET" should read --MET--. Column 4, line 6, "is HIS" should read --$AA^5$ is HIS--; line 47, "suitable" should read --suitably--. Column 9, line 18, "nnature" should read--nature-- Column 10, line 34, "bet$\alpha$" should read --beta--. Column 12, line 59 "MgSO$_4$7H2O" should read --MgSO4-7H$_2$O--. Column 15, line 5, "$10^6$M" should read --$10^{-6}$M--; line 22, "Infusior" should read -- Infusion--. Column 16, line 3, cancel beginning with "2. The peptide of" to and including "VAL or LEU" at line 18, and insert the following claim:

2. The peptide of claim 1 wherein:
$AA^1$ is LYS, GLU, or GLN;
$AA^2$ is VAL or LEU;
$AA^3$ is ASP, TYR, or GLU;
$AA^4$ is VAL, MET, ILE, or LEU;
$AA^5$ is TYR, HIS, or GLU;
$AA^6$ is ALA, PRO, or SER; and
$AA^7$ is VAL or LEU.

Signed and Sealed this

Twenty-sixth Day of December, 1989

Attest:

JEFFREY M. SAMUELS

Attesting Officer     Acting Commissioner of Patents and Trademarks